United States Patent [19]

Pickett

[11] Patent Number: 4,700,600

[45] Date of Patent: Oct. 20, 1987

[54] MICROTOME DISPOSABLE BLADE APPARATUS

[76] Inventor: John E. P. Pickett, 3323 Pinafore Dr., Durham, N.C. 27705

[21] Appl. No.: 834,351

[22] Filed: Feb. 28, 1986

[51] Int. Cl.$^4$ ............................................. G01N 1/06
[52] U.S. Cl. ...................................... 83/165; 83/699; 83/915.5
[58] Field of Search .............. 83/698, 699, 856, 915.5, 83/651, 162, 165, 166; 30/338

[56] References Cited

U.S. PATENT DOCUMENTS

| 840,748 | 1/1907 | Cafferty, Jr. ........................... 30/338 |
| 3,599,523 | 8/1971 | Pickett ................................... 83/412 |
| 3,699,830 | 10/1972 | Pickett ................................ 83/915.5 |
| 3,733,948 | 5/1973 | Pickett ................................... 83/698 |
| 4,207,790 | 6/1980 | Endo ..................................... 83/698 |
| 4,472,989 | 9/1984 | Endo ................................... 83/915.5 |

FOREIGN PATENT DOCUMENTS 2732001  2/1979  Fed. Rep. of Germany ..... 83/915.5

Primary Examiner—Paul A. Bell
Assistant Examiner—Hien H. Phan
Attorney, Agent, or Firm—B. B. Olive

[57] ABSTRACT

A microtome apparatus includes a disposable blade holder adapted to receive both thick and thin blades and for cutting frozen sections to mount an anti-roll plate assembly utilizing a magnet as the holding mechanism. Blades of different width are dispensed from an associated improved dispenser.

32 Claims, 46 Drawing Figures

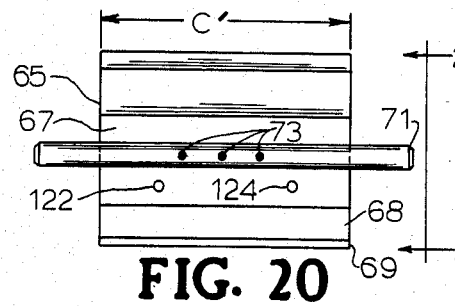
FIG. 20
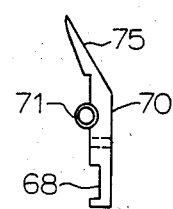
FIG. 21
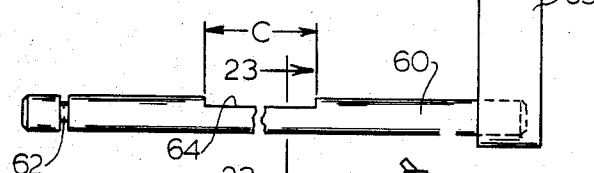
FIG. 22
FIG. 23
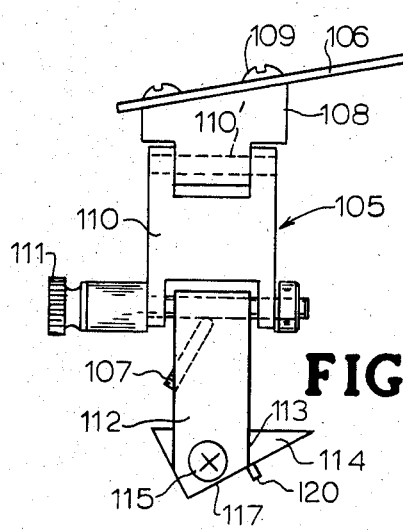
FIG. 24
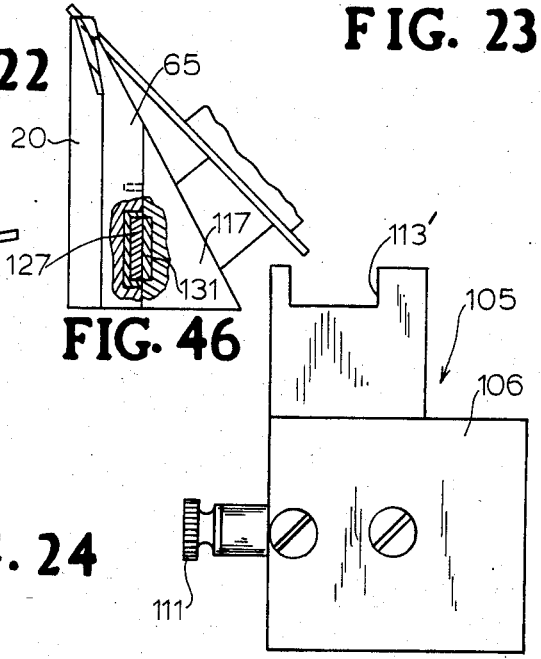
FIG. 46
FIG. 25
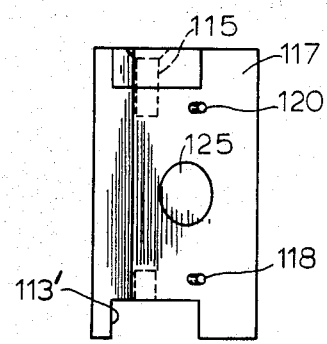
FIG. 26
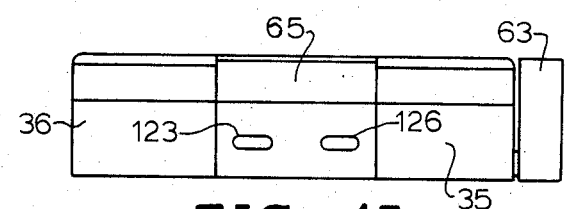
FIG. 45

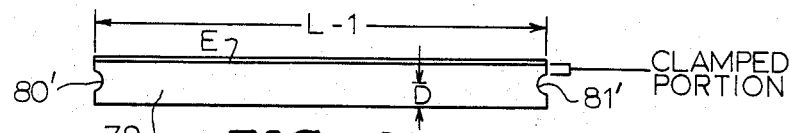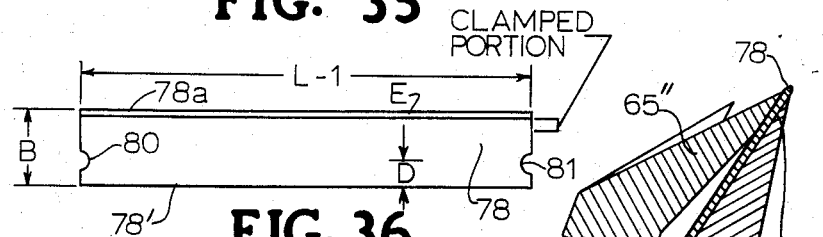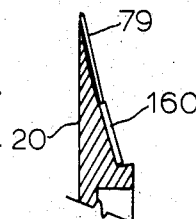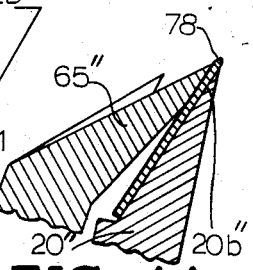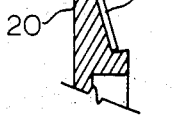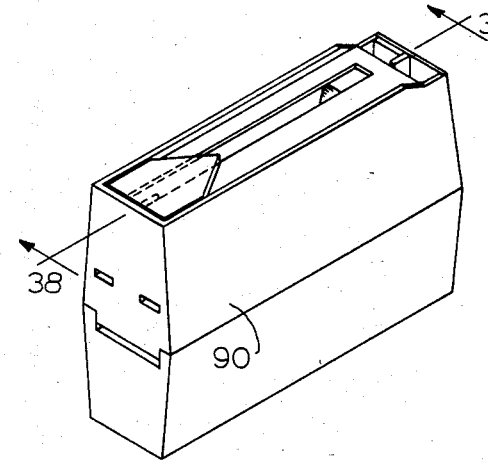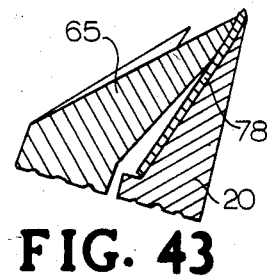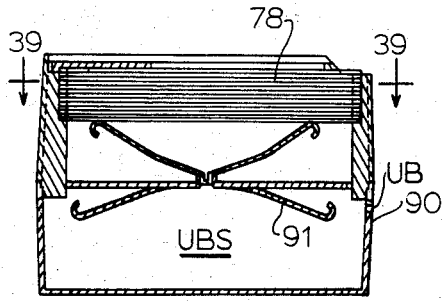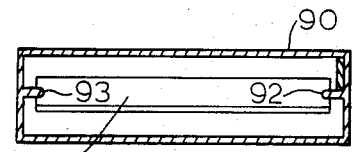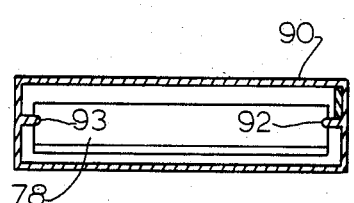

MICROTOME DISPOSABLE BLADE APPARATUS

DESCRIPTION

1. Technical Field

The invention relates to microtome knives or blades and knife or blade holders and particularly to disposable blade and disposable blade holders.

2. Background Art

As fully explained in applicant's prior U.S. Pat. Nos. 3,599,523, 3,699,830 and 3,733,948, the use of relatively thin, flexible disposable blades in microtomes has many advantages over use of the conventional, relatively thick, inflexible, microtome knife which required expensive and time-consuming resharpening. Reference may be made to the cited patents for an explanation of the prior art and background leading to the present invention.

Relatively wide disposable blades are conventionally referred to as "high" blades and relatively narrow width blades are referred to as "low" blades. Thus, both wide or high blades as well as narrow width or low blades are employed in microtome cutting.

It has been recognized that certain microtome operations are best suited when a relatively wide, e.g., 0.498 inch width, and thick, e.g., 0.016 to 0.045 inch thick, disposable blade is used for the cutting operation whereas in other microtome operations, the preferred histology practice requires use of a disposable blade of the same width but relatively thin, e.g., 0.005 to 0.015 inch thick blade. Thus, blade thickness may vary between approximately 0.005 to 0.0045 inch. In other instances, it is desirable to use a disposable blade of relatively narrow width, e.g., 0.3125 inch width, and relatively thin or relatively thick as just described. The microtome disposable blade holders described in the mentioned patents accommodated to only a narrow range of differences in blade dimension and used an adjusting mechanism for accommodating to differences in blade thickness. Thus, it has been necessary to physically adjust screws in the clamping mechanism when changing from use of one width, e.g., relatively wide, and thickness of disposable blade to another of the same width but of different thickness. The same problem has been encountered when disposable blades of another width, e.g., relatively narrow, but different thickness have changed. This operation has been time consuming and introduces the risk of having to make several experimental adjustments to the blade holder in order to obtain the desired quality of cutting and in some instances the desired quality was not obtainable after such adjusting. While not shown in the mentioned prior patents, springs have been used to force the clamping plate open for a blade change. However, the prior art construction has not permitted use of blades of different thickness without having to make secondary adjustment. "Secondary adjustment" means, for example, adjustment of screws, or the like, on the disposable blade holder as distinct from "primary adjustment" which refers to adjustment of the knife clamp 13 (FIG. 1) which holds and secures the disposable blade holder. What is to be emphasized is that the required secondary adjustment of the disposable blade holder to accommodate for disposable blade thickness as encountered in the prior art has been eliminated. Thus, the present invention recognizes that it would be desirable to have a microtome disposable blade holder that could accept blades of a given width but that could readily accept either relatively thick blades or relatively thin blades of such width when opened without requiring any physical adjustment of the blade holder. In prior art blade holders, considerable breakage of disposable blades has been experienced, particularly with brittle blades which were clamped and curved over their entire surface except for the cutting edge as, for example, in FIG. 14 of United States Pat. No. 3,599,523. The present invention seeks to eliminate or minimize such breakage.

A past practice has been to store relatively wide blades in one type of disposable blade dispenser and relatively narrow blades in another type of disposable blade dispenser. The user of a microtome is often faced with the problem of having to use, for example, a wide disposable blade in a wide blade holder for one microtome operation, a relatively narrow disposable blade in a narrow blade holder for another microtome operation, and then return back to use of a relatively wide disposable blade for the next microtome operation. A more recent practice of which the present invention takes advantage is the use of a dispenser which is adapted to store and dispense either relatively wide blades or to store and dispense relatively narrow blades. Such blade dispensers for disposable microtome blades are typically made very much like the conventional blade dispenser for single edge razor blades used in ordinary face shaving and sold under such well-known trademarks as Schick, Gillette, and the like. The end notches as in FIG. 11 of U.S. Pat. No. 3,699,830 in past practice were not standardized with respect to location for dispensing from the same type dispenser though in more recent practice they have been so standardized. A dispenser construction useful for background is illustrated in U.S. Pat. No. 4,207,790 in association with a microtome disposable blade holder of a construction different from those illustrated in applicant's previously-identified U.S. patents. It is thus recognized that it would be desirable both from the viewpoint of the manufacturer as well as the user of blades of substantial variation in width to provide a disposable blade holder system for microtomes in which the wide and narrow width blades and their dispenser were constructed so that both wide and narrow blades could be stored and dispensed from a common type dispenser and a dispenser having improved means for storing used blades as later described. Also, as contrasted with the blade holder of U.S. Pat. No. 4,207,790, it would be desirable to avoid the need for using screws to tighten and loosen the blade for a blade change.

In another aspect of experience gained from continuous use of disposable blades and microtomes in cryostat, frozen section, cutting, it has also been recognized that further improvements are needed with respect to mounting an anti-roll plate for preventing the cut, frozen tissue section from being rolled. Anti-roll plates as such have long been in use and are well known to those who use cryostat microtomes in histology and similar operations. U.S. Pat. No. 4,472,989 illustrates, for example, one such anti-roll plate assembly. The typical manner of supporting an anti-roll plate assembly on a microtome, knife holder or disposable blade holder is to either clamp the anti-roll plate base to the supporting structure or use screws which pass through and secure the anti-roll plate base to the supporting structure. In any event, the microtome operator is frequently faced with the problem of having to remove and install the anti-roll plate assembly for cleaning or sterilization. This becomes another time-consuming operation. With these further considerations in mind concerning the anti-roll plate assembly, it can also be seen that it would be desirable to provide an anti-roll plate assembly and a disposable blade holder such that the two could be quickly secured and quickly detached as needed.

The present invention has, among other objects, the object of providing an improved microtome disposable blade holder adapted to accept both thick and thin blades of the same width without requiring any physical adjustment to accommodate to blade thickness and with minimum blade breakage; designed so that the anti-roll plate assembly when used in cryostat work can be very quickly and accurately positioned on the disposable blade holder when needed and with equal dispatch removed from the disposable blade holder when not needed and with an associated dispenser useful for storing both new and used wide and narrow blades in the same type dispenser. These and other objects will become apparent as the description proceeds.

DISCLOSURE OF INVENTION

According to the invention, there is provided a precision machined microtome blade holder adapted to releasably receive the surgical type, single edge, disposable blade having a precision-formed, microtome-quality edge for use in both paraffin cutting and cryostat frozen section cutting of all of the various types of thick, thin, soft, hard, and dense tissue and bone specimens encountered in medical laboratory practice and the opposed edge free of the conventional guard member. The blade holder is adapted to be received by the conventional precision microtome knife clamp, so that no modification of the conventional microtome or clamp is required. Further, and significant to the present invention, the blade holder is adapted to receive and clamp in a longitudinal tensionless free manner both relatively thick blades as well as relatively thin blades of a selected width. A cam mechanism moves between a blade clamping and blade release position and in the release position a relatively thick or relatively thin replacement blade can be slid in from either side of the holder and used to eject the worn blade being replaced without disturbing the blade holder which remains clamped in position. No physical adjustment of the holder is required for accomodating to blade thickness when changing from use of one thickness of blade to use of another thickness of blade of the same width. The invention blade holder may be built to accept either relatively wide or relatively narrow disposable blades. The holder is useful in, for example, the Leitz, Reichert, L.K.B., American Optical and Lab-Tek microtomes and cryostats, all of which are well known to those skilled in the art.

Thick and thin disposable blades are made of uniform length but of different width and with a notch at each end at a standardized location enabling either wide or narrow blades to be stored in a dispenser having a mating pair of ribs engaging the notches so as to uniformly locate the blades, whether wide or narrow, in the dispenser. This arrangement, while previously used for blades within a relatively narrow range of widths, has not been used with the relatively wide range of blade widths of the invention. This arrangement thus takes advantage of a previously estblished trade practice in conjunction with the advantages of the present invention and is aimed at eliminating the need for having one type dispenser for relatively wide blades and another type dispenser for relatively narrow blades. When blades of the same width are replaced, whether with a blade of the same thickness or with a blade of different thickness, the operator can immediately resume sectioning without fear of losing some critical and thin section in the course of restarting the cutting schedule. A fixed angle of cutting is immediately established as soon as the blade is installed and clamped, and this angle is normally not required to be changed so long as the same type tissue is being cut. Yet, such angle can be quickly changed by rotating the microtome knife clamp. In the preferred form of the invention the edge portion only immediately below the ground cutting edge of the blade is curved when clamped as distinct from bending the entire blade as in applicant's prior patents and the body of the blade below such edge portion is supported unbent or the entire blade including the edge portion may be clamped flat either while supported or suspended while clamped without support. This feature reduces blade breakage and facilitates the ability of the invention blade to accept both thick and thin blades of the same width.

In another aspect of the invention, the front face of the disposable blade holder is provided with a pair of shallow holes or slots and a conventional anti-roll plate assembly is provided with a base having a magnet and a pair of guide pins adapted to be received by the disposable blade holder holes or slots to facilitate quick attachment and precise alignment of the anti-roll plate assembly on the disposable blade holder when required for cryostat frozen section cutting.

In a fourth aspect of the invention auxiliary means attachable to the blade holder are provided enabling the invention blade holder to be clamped in either a Johns Hopkins or Lab-Tek cryostat-type microtome clamp.

The foregoing and other features of the invention will become apparent as the description proceeds.

DESCRIPTION OF THE DRAWINGS

FIG. 20 is a rear elevation view of the center pivotal clamping plate assembled with its rocker shaft.

FIG. 21 is an end elevation view of the center clamping plate/rocker shaft assembly taken in the direction of line 21—21 of FIG. 20.

FIG. 22 is an elevation view of the cam shaft assembled to the operating lever.

FIG. 23 is a section view taken on line 23—23 of FIG. 22.

FIG. 24 is a side view of an anti-roll plate assembly modified according to the invention and shown removed from the blade holder.

FIG. 25 is a plan view of the anti-roll plate assembly of FIG. 24 when fully extended as in FIG. 24.

FIG. 26 is a bottom view of the base plate of the anti-roll plate assembly of FIG. 24 modified according to the invention.

FIG. 35 is a plan view of a relatively narrow width disposable blade notched according to the invention.

FIG. 36 is a plan view of a relatively wide disposable blade notched according to the invention.

FIG. 37 is a perspective view of a conventional disposable blade dispenser modified according to the invention.

FIG. 38 is a sectional elevation view taken in the direction of line 38—38 of FIG. 37.

FIG. 39 is a sectional view taken in the direction of line 39—39 of FIG. 38 with a relatively narrow width disposable blade stored.

FIG. 40 is a sectional view taken in the direction of line 39—39 of FIG. 38 with a relatively wide width disposable blade stored.

FIG. 41 is similar to FIG. 12 and illustrates a relatively-narrow width blade supported on a strip in turn supported on the blade-mounting surface ledge.

FIG. 42 is also similar to FIG. 12 and illustrates the blade-mounting surface modified with two ledges for supporting either relatively narrow width or relative-wide width blades.

FIG. 43 is an enlarged fragmentary section view of the disposable blade receiving portion of the locked holder of FIG. 7 with a relatively wide blade installed and with the edge portion only clamped and curved.

FIG. 44 is an enlarged fragmentary section view of the disposable blade receiving portion of the locked holder similar to FIG. 43 but illustrating the blade in effect suspended or unsupported and with the blade edge portion immediately below the ground, bevelled cutting edge clamped flat between two flat rather than between two mating curved surfaces as in FIG. 43.

FIG. 45 is a front elevation view of the assembled blade holder of the invention illustrating a modification wherein the anti-roll plate assembly base plate guide pins are received by slots rather than by holes as in FIGS. 3 and 33.

FIG. 46 is a sectional view similar to FIG. 7 illustrating a modification of the anti-roll plate assembly securing arrangement in which the holding magnet is embedded in the disposable blade holder.

BEST MODE FOR CARRYING OUT THE INVENTION

Figure 1:
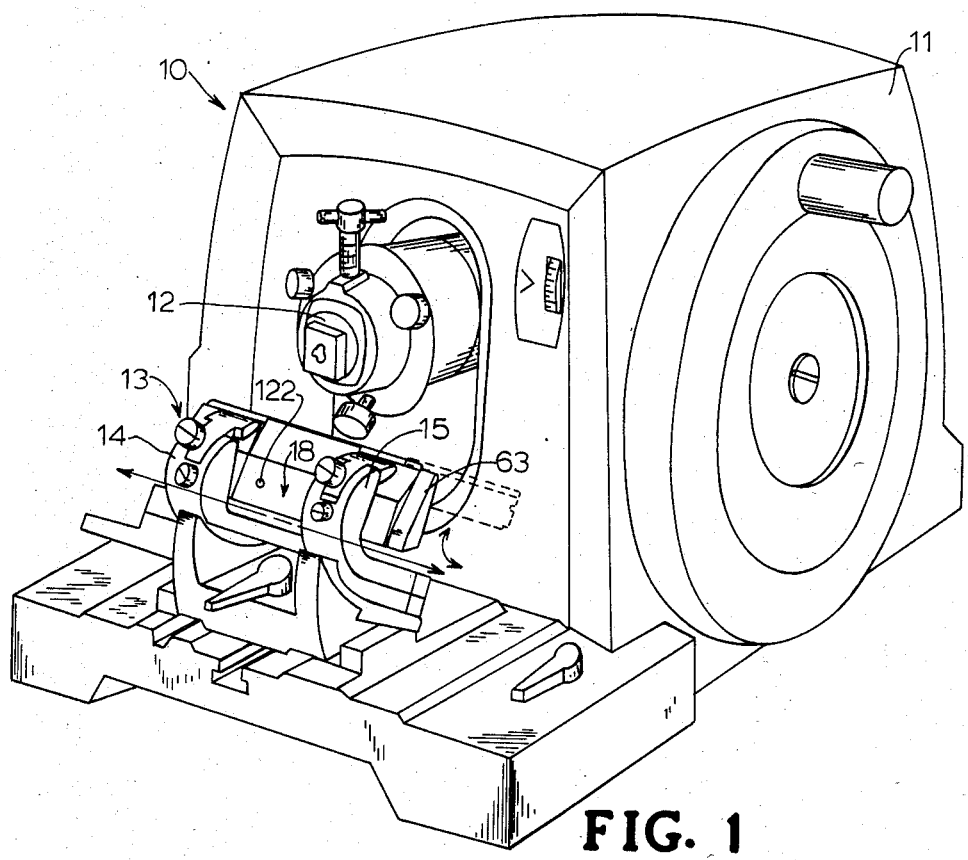
FIG. 1 is a pictorial view of a conventional microtome and knife clamp with the disposable blade holder of the invention mounted in the clamp, and in dashed lines a new replacement blade.
Figure 2:
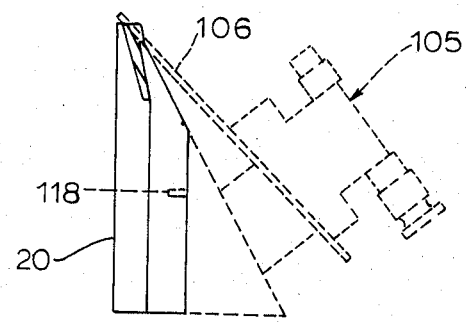
FIG. 2 is a left end elevation view of the invention blade holder showing in dashed lines a conventional anti-roll plate assembly modified according to the invention and mounted on the improved blade holder of the invention.
Figure 3:
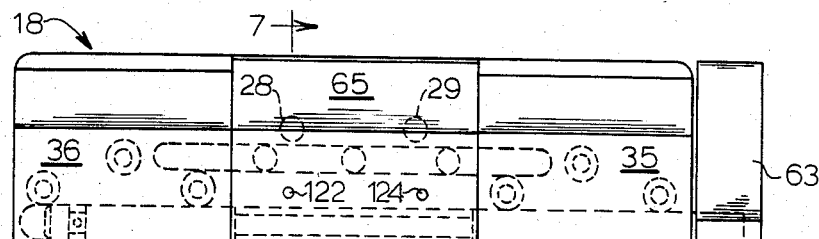
FIG. 3 is a front elevation view of the assembled blade holder of the invention.

What is taught by my prior patents as previously identified may be referred to for background for the present invention. Referring to FIG. 1, a conventional rotary microtome 10 comprises a housing 11 having the customary gearing for moving the specimen holder 12 in a vertical reciprocatory path and at the same time feeding holder 12 outwardly against a stationary disposable blade. While the described type microtome is used for illustration, it is recognized that in other microtomes relative displacement of the specimen holder and blade is obtained by advancing the blade toward the holder. The invention is useful with either type. The so-called "knife clamp" of microtome 10 used for illustration is generally indicated at 13. The conventional Johns Hopkins clamp for the American Optical Company, Spencer 820 microtome is used in illustration. However, as previously rfoted, the blade holder 18 of the invention is adapted for use, for example, in a Leitz, Reichert, L.K.B. or Lab-Tek microtome and cryostats as well as the American Optical type. Knife clamp 13 is adjustable, both rotatably and laterally as indicated by the arrows in FIG. 1 so that the cutting edge of the disposable blade of the invention can be adjusted for the proper clearance angle, tilt, and position. Knife clamp 13 has a pair of jaws 14, 15 against which the end portions of the disposable blade holder 18 of the invention are securely held in the clamp. That is, the space normally occupied by the conventional microtome knife is instead occupied by the blade holder of the invention, the invention blade width being at most a minor portion of the conventional knife width. As referred to in later description in reference to FIGS. 27-34, the present invention also provides a modified arrangement for holding the blade holder 18 of the invention in a so-called "Lab-Tek" cryostat microtome clamp in which the knife clamp clearance is somewhat larger and of a different shape than in the case of the referred-to Johns Hopkins type clamp.

Blade holder 18 may be constructed to operate with relatively wide width disposable blades of different thickness or with relatively narrow width disposable blades of different thickness or, as later described, with either. For illustration a wide width blade is assumed to be employed in respect to first-describing FIGS. 1-23 and later in connection with FIGS. 43 and 44.

The blade holder 18 of the invention in the preferred form includes a backing plate 20; a pair of right and left end clamping plates 35, 36 fixedly mounted on plate 20; a rotatable cam shaft member 60 having a manual control member 63 and a central rocker shaft-supported clamping plate 65 all of which are precisely machined preferably of stainless steel.

Support for the disposable blade, e.g., blade 78 in FIG. 36, is provided by the backing plate 20. Plate 20 resides in clamp 13 and has ends which extend outside the respective jaws 14, 15. Backing plate 20 has beginning at its uppermost edge 20a (FIGS. 10-12), a curved backing surface 20b which extends for the length of plate 20 and in use receives the clamped and curved edge portion next to and immediately below the ground, bevelled cutting edge E of the disposable blade. Curved surface 20b blends with a flat backing surface 20c which extends for the length of plate 20 and downward a predetermined distance corresponding to the width B of the disposable blade 78 being used by way of example and across the length of plate 20. As distinct from applicant's disposable blade holders in which the entire blade was curved when clamped, the present invention is based at least in part on discovering the advantage of clamping only the edge portion next to and immediately below the ground, bevelled blade cutting edge E against curved surface 20b with the rest of the blade resting on the flat backing surface 20c. The ground, bevelled cutting edge E is left exposed for cutting. Such blade edge portion clamping arrangement is found to permit clamping of both thick and thin blades of the same width when incorporated in the invention blade holder without requiring any adjustment of the blade holder clamping mechanism and with reduced blade breakage.

In one embodiment utilizing disposable blades 0.498" wide, 3.00" long and either 0.012" or 0.020" thick curve 20b was 0.12" long and formed part of an arc on a 3.00" radius R. Distance B was 0.450" and angle X was 15°. At the base of the flat surface 20c is a lengthwise extending shallow ledge 22 which acts as a stop or rest and supports the lower edge 78' of disposable blade 78 being used by way of example. A flat face 23 extends for the length of plate 20 and downward from ledge 22. Face 23 has a first set of holes 24, 25, and 26 for receiving screws to secure right end clamping plate 35; another set of holes 24', 25', 26' for receiving screws to secure left end clamping plate 36; and a third set of holes 30, 31 which extend partially through the thickness of plate 20 for receiving and seating a pair of springs 28, 29 as later described. Near the bottom edge of plate 20 there is a semicircular groove 32 which extends into and lengthwise of plate 20 and terminates at an edge portion 32a within the body of plate 20. Immediately adjacent the bottom of plate 20 and extending upwardly to the bottom edge of groove 32 is a small flat lengthwise extending face area 33. The back of plate 20 is formed flat which provides a flat back clamping surface for clamping the blade holder 18 of the invention in the jaws 14, 15 of the conventional knife clamp 13. Another centrally-located groove 34 extends into and lengthwise of backing plate 20 to receive the rocker shaft 71 on which the central pivotal clamping plate 65 pivots.

Opening and closing of blade holder 18 is controlled by a rotatable cam shaft 60 which mounts in groove 32 with axial movement being prevented by means of a pin 61 (FIG. 10) fixed in backing plate 20 and slidably engaging slot 62. Shaft 60 mounts a manual control member 63 for the operator to use in rotating cam shaft 60. Shaft 60 also has a flat side 64 cut therein which permits shaft 60 to cam central pivotal clamping plate 65 into open and closed positions. The length C of flat side 64 at least equals and preferably exceeds the width C' of plate 65.

While not illustrated, it is noted that shaft 60 may be lengthened if desired so as to offset control member 63, to the right as viewed in FIG. 1, sufficiently to allow blade guards to be placed on the non-cutting but exposed blade edges above plates 35, 36. Such blade guards are known and are sometimes employed as an extra safety precaution.

Clamping plates 35, 36 are fixedly mounted on plate 20 to form an essentially integral structure. Clamping plate 35 has a flat inner face 35a and clamping plate 36 has a flat inner face 36a, both of which match the flat face 23 of plate 20. A semicircular groove 37 extends across the full width of plate 35 and a similar semicircular groove 38 extends partially across plate 36, both of which grooves 37 and 38 mate with groove 32 of plate 20 to form circular openings between plates 35, 36 and plate 20 for receiving the ends of shaft 60 in a snug rotatable relation. Upward a predetermined distance from the respective grooves 37, 38 are respective inwardly angled flat inner surfaces 35b and 36b. The respective inner surfaces 35b and 36b extend upwardly a predetermined distance so that the respective uppermost edges 35c and 36c are aligned with the edge 20a of backing plate 20. Respective front sloping clamping faces 35d and 36d join respective flat front faces 35e and 36e. Inner face 35a of plate member 35 has three threaded holes 45, 46 and 47 mating respectively with threaded holes 24, 25 and 26 of plate 20. Plate 36 has a similar set of threaded holes 48, 49, 50 mating respectively with holes 24', 25' and 26' of plate 20. Holes 24, 25 and 26 as well as holes 24', 25' and 26' in back plate 20 are countersunk (FIG. 11) so that the screw heads of the screws 39 (FIG. 34) securing plates 35, 36 and 20 together will remain flush with the flat back face of backing plate 20. Exposed screw heads on the front of the blade holder have thus been eliminated and which reduces the potential for laboratory contamination. Clamping plates 35, 36 hold the ends of cam shaft 60 in place but with freedom for shaft 60 to rotate and with lateral or axial motion being prevented by the previously-mentioned pin 61 engaging slot 62. Clamping plates 35, 36 also serve the function of rotatably and snugly receiving in the respective grooves 40, 41 the ends of rocker shaft 71 secured to the back of central pivot and clamping plate 65.

The central pivotal clamping plate 65 fits within the lateral spacing of clamping plates 35 and 36 and provides means for clamping the edge portion immediately below the ground, bevelled cutting edge E of the disposable blade in curved relation and the remainder of the blade in flat relation. Plate 65 has a curved, convex surface 66 which mates with the convex surface 20b of backing plate 20 and a flat surface 66' which extends downward from surface 66 and in use mates with the opposing portion of flat surface 20c of plate 20. A connecting flat surface 67 below ledge 66" mates flat surface 23 of plate 20 below ledge 72. A square-shaped slot 68 is cut into surface 67 above the bottom edge of plate 65. Square slot 68 overlies and aligns with the middle portion of semicircular groove 32 and and also aligns with groove 37 of plate 35 and groove 38 to form an opening for substantially the full length of the holder 18 and in which resides shaft 60. Slot 68, unlike grooves 32, 37 and 38 has straight side walls with no curvature and is designed so that flat side 64 of shaft 60 is substantially vertical when the holder 18 is open as in FIG. 8 and substantially horizontal when closed as in FIG. 7. Springs 28, 29, mounted in holes 30, 31 (FIG. 10), are compressed when holder 18 is closed and expanded when holder 18 is open.

A flat surface 69 on plate 65 mates with flat surface 33 of backing plate 20. A flat exterior surface 70 on plate 65 generally aligns with exterior faces 35e, 36e of clamping plates 35, 36 when holder 18 is closed. A front tapered angled surface 75 extends upwardly from surface 70 to the upper edge 66a of plate 65 and it is this surface which guides the cut tissue in paraffin cutting when an anti-roll plate is not used as in frozen section cutting. Shaft 71 is spot welded by welds 73, held by screws, or otherwise secured to plate 65 in the groove 72 with the outwardly extending ends of shaft 71 being received respectively by the mating grooves 40 and 41 in respective plates 35 and 36. Thus, plate 65 forced outwardly by springs 28, 29 is free to rotate or rock very precisely around the precisely located axis of shaft 71 with the ends of the shaft 71 being retained in the holes formed by the respective grooves 40, 41 and mating groove 34 in backing plate 20.

As previously stated, precision-sharpened disposable blades suitable for use with the invention but without the usual guard member are manufactured and sold under various trademarks such as Personna and Weck. The preferred disposable blade is of a standardized length $L_1$ greater than the length C' (FIG. 20) of pivotal plate 65 and is substantially greater in length than standard single or double edge razor blades so that cuts can be taken from large specimen blocks. That is, a specimen block up to at least the length C' can be cut. Length $L_1$ is standardized for both relatively thick and thin blades 78 of relatively wide width (FIG. 36) as well as for relatively thick and thin blades 79 of relatively narrow width (FIG. 35). Each of the disposable blades, whether of relatively wide width 78 or relatively narrow width 79 is provided with a pair of notches indicated at 80, 81 and 80', 81' centered on a line offset a standard distance D from the base edge of the blade. The minimum width blade suited to the invention is generally governed by the minimum width strip which can be sharpened by the manufacturer and such minimum width may be 0.3125" or less whereas the maximum wide width blade according to current practice could be 0.498" or more. Thicknesses are expected to vary between approximately 0.005" to 0.045".

As part of the microtome diposable blade system provided by the invention, the dispenser 90, generally of conventional construction, is modified so as to provide a pair of vertical ribs 92, 93 within its storage chamber adapted to receive the previously-mentioned pair of notches 80, 81 or 80', 81' in the disposable blades. Thus, dispenser 90 is adapted to receive and dispense a stack of blades 78 as in FIG. 38 which are relatively thick or thin and relatively wide in width as well as a stack of blades 79 which are relatively thick or thin and relatively narrow in width. Used blades are inserted through a suitable slot UB (FIG. 38) into a used blade storage chamber UBS and once stored are prevented, as a safety precaution, from being inadvertently discharged through slot UB by means of a resilient spring 91. Spring 91 is pushed slightly upward when each used blade is inserted and then restores itself to a position which restricts any used blade from passing back out through slot UB. The entire dispenser 90 may be disposed of once all blades have been used.

Reference will now be directed to the operation of the disposable blade and blade holder of the invention as thus far explained. Once the holder is assembled as described and illustrated in FIG. 1, microtome clamp 13 is adjusted or tilted into an approximate 15° position towards feeding holder 12. The disposable blade holder 18 of the invention is slid into the clamp 13 endwise so that clamping plate 35, 36 are in central alignment with jaws 14, 15. Once in position, jaws 14, 15 are tightened on sloped surfaces 35d and 36d of clamp plates 35, 36 and effectively lock the blade holder in clamp 13. Finger grip or control member 63 is turned so that flat side 64 of shaft 60 is substantially vertical and in a non-camming position as in FIG. 8. With shaft 60 in this unlocking position, and central plate 65 forced outwardly by means of the illustrated compression springs 28, 29, the disposable blade, e.g., a relatively wide and thick blade 78, is slid into the holder 18 from the side so that it rests on ledge 22 with the holder edge portion 20a immediately below the exposed ground, bevelled cutting edge E located between the respective concave sloping surface 20b on plate 20 and convex sloping surface 66 on plate 65 and the body of the blade between plate 20, surface 20c and plate 65, surface 66'. It should be noted here that plates 35, 36 and 20 form fixed flat walled blade shaped slots $S_1$, $S_2$ (FIG. 5) through which the disposable blade, whether thick or thin, can be slid from the side in a snug slidable fit. Two slots $S_1$, $S_2$ ensure the ability to push out the old blade with the new blade. Once the disposable blade is in position, shaft 60 is rotated by turning finger grip 63. As shaft 60 is rotated, flat side 64 is rotated a corresponding amount and the circular portion of shaft 60 is brought into contact with slot 68 which causes central pivotal plate 65 to compress springs 28, 29 and be pivoted around the axis of rocker shaft 71. Convex surface 66 is moved forward against substantially the whole plane of the disposable blade edge portion, e.g., edge portion 78a (FIG. 38) immediately below the exposed ground, bevelled cutting edge E so that the disposable blade edge portion immediately below the cutting edge E is bent and curved uniformly around a longitudinal axis until it is against concave surface 20b and the body of the blade is supported flat against backing surface 20c of plate 20 in a longitudinally tensionless free manner as by FIG. 43. At this point, shaft 60 assumes a self-locking position holding the disposable blade edge portion immediately below the cutting edge curved, stiffened and angled for proper cutting by the cutting edge and the body of the blade supported flat, unclamped and resting on ledge 22 as in FIG. 43.

Figures 7, 8, 9:
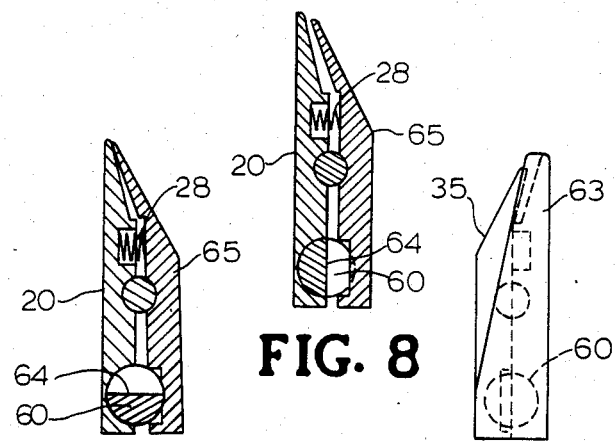
FIG. 7 is a sectional view taken on lines 7—7 of FIG. 3 with the blade holder cammed to a closed blade clamping position but without a blade.
FIG. 8 is a sectional view taken on lines 7—7 of FIG. 3 with the blade holder cammed to an open blade clamping position.
FIG. 9 is a right end elevation view of the disposable blade holder of the invention.
Figure 10:
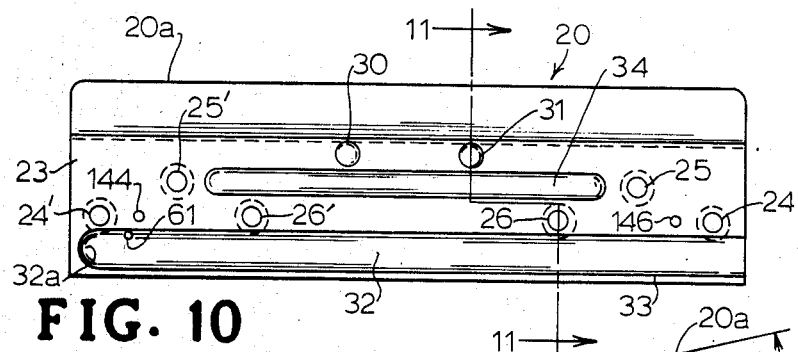
FIG. 10 is a front elevation view of the backing plate removed from the blade holder.
Figure 11:
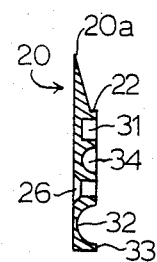
FIG. 11 is a sectional view taken on line 11—11 of FIG. 10.
Figure 12:
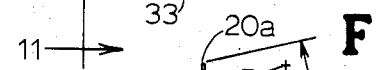
FIG. 12 is a highly enlarged sectional view of the blade mounting surface portion of the backing plate.
Figure 13:
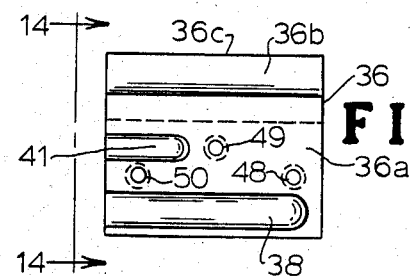
FIG. 13 is a rear elevation view of the right end clamping plate removed from the blade.
Figure 14:
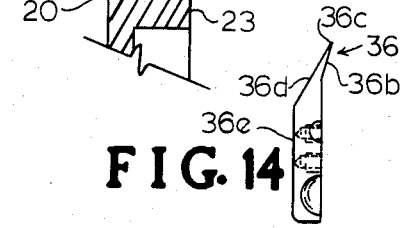
FIG. 14 is an end elevation taken in the direction of line 14—14 of FIG. 13.
Figures 15, 16:
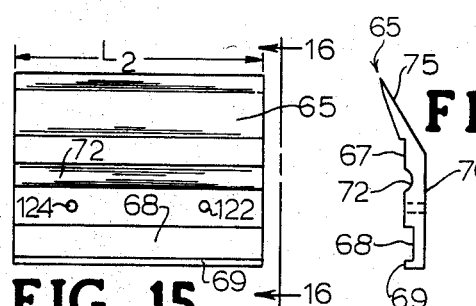
FIG. 15 is a rear elevation view of the center pivotal clamping plate removed from the holder.
FIG. 16 is an end elevation view taken in the direction of line 16—16 of FIG. 15.
Figure 17:
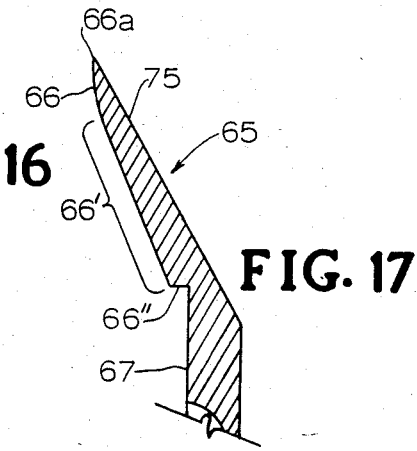
FIG. 17 is a highly enlarged sectional view of the clamping surface of the center pivotal clamping plate of FIG. 16.
Figure 18:
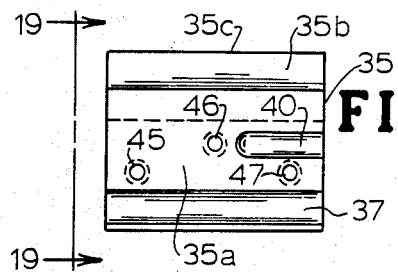
FIG. 18 is a rear elevation view of the left end clamping plate removed from the holder.
Figure 19:
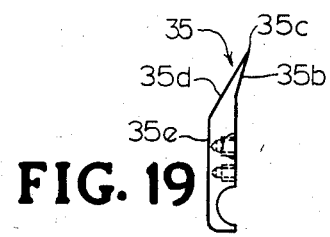
FIG. 19 is an end elevation view taken in the direction of line 19—19 of FIG. 18.
Figure 27:
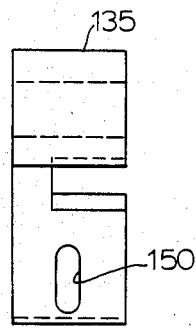
FIG. 27 is a front view of a left end insert useful in mounting the invention blade holder in the type microtome clamp in which the knife clamp space is larger than the space occupied by the invention blade holder.
Figure 28:
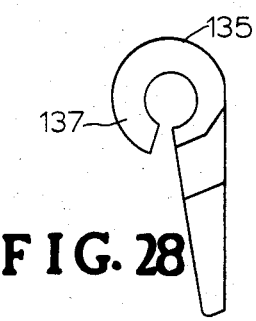
FIG. 28 is an end view of the left end insert.
Figure 29:
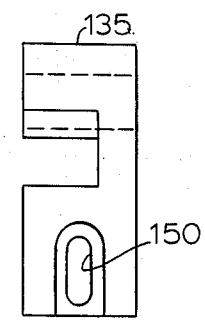
FIG. 29 is a front view of the left end insert.
Figure 30:
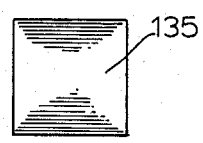
FIG. 30 is a top view of the insert.

The disposable blade, once dulled, can be replaced by reversing finger grip 63 so as to turn cam member 60 back to the FIG. 8 position which releases the blade. Dispenser 90 is then employed to install a new disposable blade and at the same time to push the used blade endwise out of the holder as a new blade is being pushed in. The used blade is stored in chamber UBS (FIG. 38)

as previously explained. Of significant importance is the fact that a thick blade of one width can be replaced by a thin blade of the same width without removing the holder 18 from the clamp 13 or adjusting the holder 18 for blade thickness which in turn eliminates loss of valuable sections due to retrimming of the section block. Noticeably, the invention blade holder construction eliminates the need for any blade holder adjustment to accomodate for different blade thickness. Therefore, no such adjustment means is provided. Also, the disposable blades can be replaced from either side of the holder 18 as preferred by the individual operator. Replacement blades whether thick or thin but of the same width are easily installed by simply turning cam shaft 60 into an "unlocking" position and inserting a new blade from either side, usually determined by the operator being left or right handed and without requiring adjustment of the blade holder 18. Blade thickness and curvature and the presence of springs 28, 29 ensure self-locking of shaft 60. Blade breakage is minimized.

In another aspect of the invention for frozen section cutting, there is illustrated in FIGS. 2 and 24–26 a conventional anti-roll plate assembly 105 including an anti-roll plate 106 for receiving the tissue to prevent its rolling, a support member 108 on which anti-roll plate 106 is secured by screws 109, a pivotal connecting member 110 connected by pin 110' to member 108 and of conventional construction secured by positioning screw 111 to support arm 112 secured in slot 113 to a modified base 114 by means of a screw 115. Set screw 107 is tightened when desired to maintain the setting of screw 111. An alternate slot 113' is provided with a threaded hole 116 when it is desired to support arm 112 on the opposite side of base 114. Base 114 in turn has a flat surface 117 with a pair of protruding locating pins 118, 120 to be received by mating holes 122, 124 on plate 65. Blade holder 18 is preferably of stainless steel construction and is therefore ferromagnetic in nature, whereas base 114, member 108, member 110 and arm 112 are preferably made of aluminum and are therefore not ferromagnetic in character. At least one relatively strong, permanent magnet 125 is centrally embedded in base plate 112 and provides a means with locating pins 118, 120 installed for rigidly but detachably securing and precisely positioning the anti-roll assembly 105 on the blade holder 18 of the invention. While not illustrated, it is recognized that plural magnets could be employed if desired. Thus, the need for conventional clamps to hold the anti-roll assembly 105 on blade holder 18 in place, the use of screws, or the like, are avoided by this new magnetic holder for the anti-roll plate assembly 105 when required for frozen section cutting.

In a modification of the anti-roll assembly 105, magnet securing means illustrated in FIG. 45, pins 118, 120 are received by slots 123, 126. Thus, in this modification the assembly 105 can be quickly installed and precisely adjusted as required.

In a further modification illustrated in FIG. 46, plate 65 mounts a magnet 127 in a surrounding insulator 129 and the base plate 117 of the anti-roll assembly incorporates an embedded stainless steel plate 131 adhered to base plate 117 to effect securement.

Figure 4:
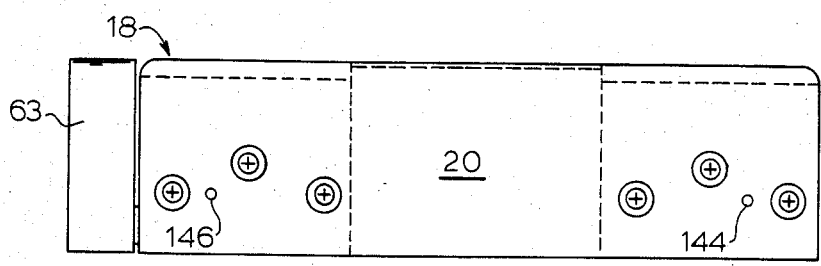
FIG. 4 is a rear elevation view of the assembled blade holder of FIG. 3.
Figure 5:
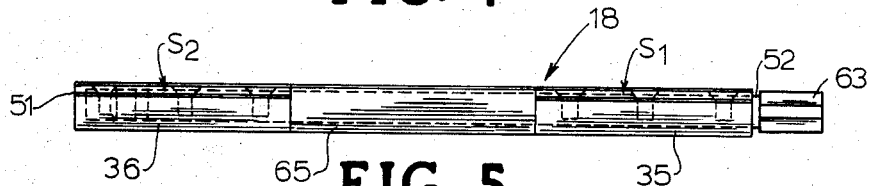
FIG. 5 is a top view of the blade holder of FIG. 3 in a closed position.
Figure 6:
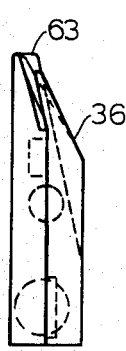
FIG. 6 is a left end view of the blade holder.
Figure 32:
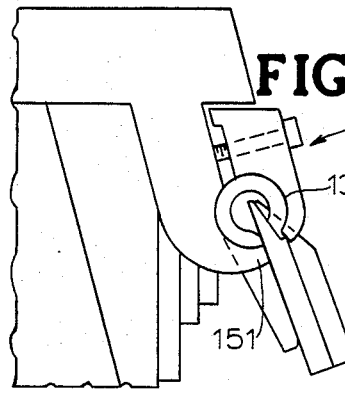
FIG. 32 is a partial end elevation view showing the left end insert on the blade holder and clamped in the particular microtome clamp to which the insert is adapted.
Figure 31:
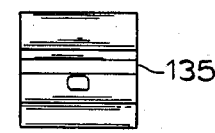
FIG. 31 is a bottom view of the insert.
Figure 33:
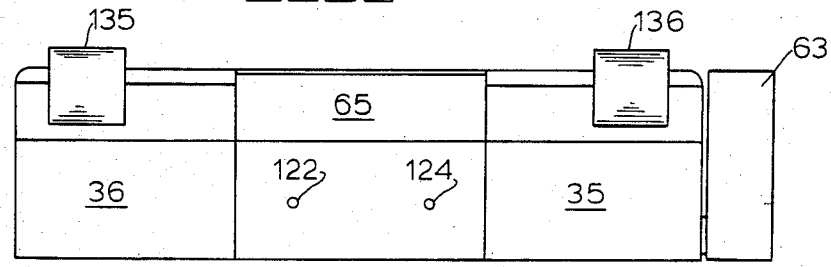
FIG. 33 is a front elevation view of the invention blade holder removed from the microtome with a pair of the inserts installed at the left and right ends.
Figure 34:
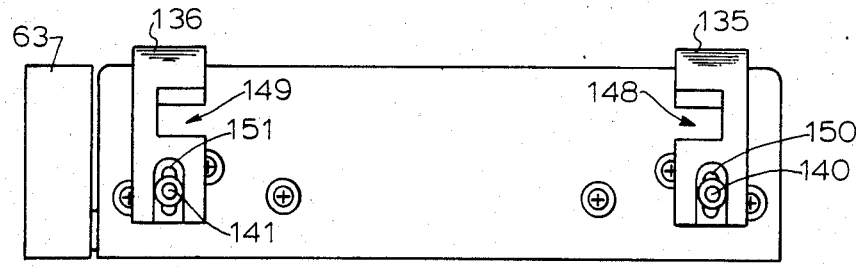
FIG. 34 is a rear elevation view of the invention blade holder of FIG. 33 with the right and left end inserts installed.

In another aspect of the invention there is also provided a pair of inserts 135, 136 illustrated in FIGS. 27–34 enabling the blade holder 18 of the invention to be used in a Lab-Tek type of cryostat microtome clamp 132 in which the space for receiving the improved holder 18 of the invention is larger and of different shape than the Johns-Hopkins type clamp. Thus, when the Lab-Tek type clamp 132 is used, the two inserts 135, 136 are secured by means of set screws 140, 141 in respective threaded holes 144, 146 provided on the back face of back plate 20 (FIG. 4). The respective set screws 140, 141 are received in respective slots 150, 151. Since inserts 135 and 136 are of similar construction only the construction of insert 135 is shown in detail in FIGS. 27–31 it being noted however in FIG. 34 that slot 148 of insert 135 is oriented oppositely from slot 149 of insert 136 to accomodate the corresponding clamp arms 151 (FIG. 31). Each of the respective inserts 135, 136 of the general construction shown in FIGS. 27–31 is provided with an open slotted C section 137 adapted to overlie the mated back plate 20 and respective plates 35, 36, as best seen in FIGS. 32–33. A solid and secure clamping in the Lab-Tek type cryostat microtome clamp 132 is thus achieved.

The description thus far has assumed that relatively wide blades 78 in varying thickness are being used. The invention however readily accomodates to use of the relatively narrow blades 79 in varying thickness in the same blade holder used for relatively wide blades, in a blade holder made specially for relatively narrow blades of varying thickness or in a blade holder in which both relatively wide and relatively narrow blades of varying thickness may be used in the same holder.

First, it may be observed that simply by making the dimensions of faces 20b and 20c of plate 20 and the dimensions of faces 66 and 66' of plate 65 correspond to the narrow width blade 79, the blade holder 18 is readily modified to accept relatively narrow width blades of varying thickness. Alternatively the narrow blades 79 of some relatively thick or relatively thin thickness may be mounted on a removable, thin metal plate 160 of appropriate size as in FIG. 41 and clamped while so mounted using the same blade holder construction as for the relatively wide blade 78.

In another construction, modified plate 20', as in FIG. 42, accommodates a relatively narrow width blade of selected thickness seated on ledge 165 or a relatively wide width blade of selected thickness seated on ledge 166. Curved surface 20b' of curvature comparable to that of curved surface 20b enables the cutting edge portion only of the blade to be bent and curved when clamped whether the blades are relatively narrow as in FIG. 35 or relatively wide as in FIG. 36. Clamping plate 65 may otherwise remain in the form previously described and in conjunction with the modified plate 20' may thus be employed to clamp only the edge portion immediately below the ground, bevelled cutting edge E of either a relatively narrow or a relatively wide width blade against the modified plate 20'.

The most significant aspect of the invention is regarded as being the ability to use the improved and precisely located rocker shaft supported clamping plate 65 to clamp either thick or thin blades without requiring adjustment of the holder to accommodate for blade thickness and utilizing a lever/shaft cam action to open and close the holder. For certain types of cutting it is further recognized that the edge portion immediately below the ground, bevelled cutting edge E could be clamped flat as in FIG. 44 with the blade, in effect, unsupported or suspended and clamped between two opposed flat cutting edge portion clamping surfaces 20''b of modified plate 20'' and 66'' of modified clamping plate 65'' and still retain the advantage of the lever/cam shaft positioned precisely located rocker shaft supported clamping plate of FIGS. 1-23.

What is claimed is:

1. A microtome apparatus comprising, in combination:
   (a) a specimen holder mechanism including means for holding said specimen, means for applying a reciprocating motion to said specimen relative to and for cutting in a vertical plane and for positioning the specimen and holder relative to the cutting plane;
   (b) a knife clamp adapted to clamp a conventional non-disposable microtome knife, said clamp being movable laterally and tiltable with respect to the specimen for appropriate precision positioning of the knife cutting edge;
   (c) a substantially rectangular disposable blade of a selected uniform width and thickness, having one longitudinal edge precision sharpened to microtome knife quality for cutting and the opposed edge free of the conventional guard member, being of substantially less flexibility than the conventional double edge wafer blade while being held clamped; and
   (d) a holder for said disposable blade adapted to being received and held in said conventional knife clamp, comprising:
      (i) a first horizontally disposed block member having a pair of end portions with knife clamp surfaces enabling said holder to be clamped within said knife clamp and providing between said knife clamp surfaces and proximate said cutting plane a blade clamp backing surface for receiving said blade during loading in a non-curved relation and against which the cutting edge portion of one side of said blade may be fixedly held during cutting to place the cutting edge thereof in said cutting plane, each of said end portions having a slot shaped to fit and slidably receive said blade whether relatively thick or relatively thin for loading from either corrresponding end of said block member;
      (ii) a blade clamping member comprising a second block member having a slight and precise amount of inward-outward movement and mounted centrally of said first block member on a rocker arm rotatable in and snugly retained by said first block member end portions, said second block member having a clamping surface mating said first block member backing surface and said movement adapting said second block member at the end of its outward movement to provide with said backing surface a central slot forming a continuation of said end portion slots to slidably receive said blade and at the end of its inward movement being adapted to contact and clamp a lengthwise extending edge portion located immediately below the sharpened cutting edge of the other opposite one side of said blade in a longitudinally tensionless free manner between said backing and clamping surfaces and to properly position the said cutting edge thereof;
      (iii) opening means operative on said clamping member when unclamped to force said clamping member outwardly; and
      (iv) a manually operated rotatable camming member mounted on said holder, said camming member being effective when rotated in one direction to cam said second block member and pivot said second block member about the axis of said rocker arm in said slight outward movement so as to effect said central slot and release said blade for replacement and in an opposite direction to cam said second block member in said slightly inward movement against the force of said opening means so as to clamp at least said edge portion of said blade while leaving the said sharpened cutting edge precisely positioned for cutting.

2. A microtome apparatus as claimed in claim 1 wherein said first block member comprises a base member and a pair of removable end members forming portions of said end portions.

3. A microtome apparatus as claimed in claim 2 wherein:
   (a) said backing surface comprises a concave surface;
   (b) said clamping surface comprises a convex surface; and
   (c) said camming member is effective in said slightly inward movement of said second block member to clamp and curve the said edge portion of said blade between said backing and clamping surfaces.

4. A microtome apparatus as claimed in claim 3 wherein said blade clamping surface includes a ledge for supporting the base of said blade.

5. A microtome apparatus as claimed in claim 1 wherein:
   (a) said backing surface comprises a concave surface;
   (b) said clamping surface comprises a convex surface; and
   (c) said camming member is effective in said slightly inward movement of said second block member to clamp and curve the said cutting edge portion of said blade around a longitudinal axis between said backing and clamping surfaces.

6. A microtome apparatus as claimed in claim 5 wherein said blade clamping surface includes below said concave surface a flat surface against which one flat side of the body of said blade below the said edge portion may rest during cutting.

7. A microtome apparatus as claimed in claim 5 wherein said convex and concave surfaces are formed to clamp and curve only the said edge portion of said blade below the said sharpened cutting edge thereof and other portions of said blade clamping second block member and first block member are formed to support without clamping all but said edge portion of said blade in flat relation.

8. A microtome apparatus as claimed in claim 5 wherein said opening means comprises spring means mounted between said first block member and said clamping member.

9. A microtome apparatus as claimed in claim 1 wherein:
   (a) said backing surface comprises a flat surface;
   (b) said clamping surface comprises a flat surface; and
   (c) said camming member is effective in said slightly inward movement of said second block member to clamp the said edge portion of said blade flat between said backing and clamping surfaces.

10. A microtome apparatus as claimed in claim 9 wherein said opening means comprises spring means mounted between said first block member and said clamping member.

11. A microtome apparatus as claimed in claim 1 including in anti-roll plate assembly with a base member, magnet securing means embedded in said base member and means on said clamping member for precisely locating said base member thereon and utilizing said magnet securing means for securing said anti-roll assembly on said holder.

12. A microtome apparatus as claimed in claim 11 wherein said magnet securing means comprises a magnet embedded in said base member.

13. A microtome apparatus as claimed in claim 11 wherein said means on said blade clamping member for precisely locating said base member thereon includes a pair of holes on the outer surface of said blade clamping member and said anti-roll assembly includes a pair of pins mating said holes and locating said base member.

14. A microtome apparatus as claimed in claim 13 wherein said magnet securing means comprises a single magnet embedded in said base member.

15. A microtome apparatus as claimed in claim 11 wherein said means on said blade clamping member for precisely locating said base member thereon includes a pair of slots in said blade clamping member and said anti-roll assembly includes a pair of pins mating said slots and locating said base member.

16. A microtome apparatus as claimed in claim 11 wherein said magnet securing means comprises a ferromagnetic plate embedded in said base member and said means on said blade clamping member for precisely locating said base member thereon includes a magnet embedded therein and attracted to said ferromagnetic plate.

17. A microtome apparatus as claimed in claim 1 including a pair of insert members removably secured on the ends of said first block member and formed for effectively enlarging the size of said end portions and for being received and clamped in a corresponding size of said knife clamp.

18. A microtome apparatus as claimed in claim 1 wherein said blade clamping surface includes a ledge for supporting the base of said blade.

19. A microtome apparatus as claimed in claim 1 wherein said blade clamping surface is formed for receiving a relatively wide width said blade and including a strip member supported on said ledge for in turn supporting a relatively narrow width blade thereby enabling a said narrow width blade to be clamped on said blade clamping surface formed for receiving a relatively wide blade.

20. A microtome apparatus as claimed in claim 1 wherein said blade clamping surface includes upper and lower ledges for respectively supporting relatively narrow width and relatively wide width said blades.

21. A microtome apparatus as claimed in claim 1 wherein said opening means comprises spring means mounted below said clamping and backing surfaces and above said rocker arm.

22. A microtome disposable blade holder for holding a substantially rectangular disposable microtome blade of a selected uniform width and thickness, having one longitudinal edge precision sharpened to microtome knife quality for cutting and the opposed edge free of the conventional guard member and of substantially less flexibility than the conventional double edge wafer blade, said holder being adapted to being received and held in a conventional microtome knife clamp adapted to clamp a conventional non-disposable microtome knife and movable laterally and tiltable with respect to the specimen being cut for appropriate precision positioning of the knife cutting edge in the cutting plane, said holder comprising:

(a) a first horizontally disposed block member providing a pair of end portions with knife clamp surfaces enabling said holder to be clamped within the knife clamp and providing between said knife clamp surfaces and proximate said cutting plane a blade clamp bahking surface for receiving a disposable blade during loading in a non-curved relation and against which the cutting edge portion of one side of said blade may be fixedly held during cutting to place the cutting edge thereof in the cutting plane, each of said end portions having a slot shaped to fit and slidably receive said blade whether relatively thick or relatively thin for loading from either corrresponding end of said block member;

(b) a blade clamping member comprising a second block member having a slight and precise amount of inward-outward movement and mounted centrally of said first block member on a rocker arm rotatable in and snugly retained by said first block member end portions, said second block member having a clamping surface mating said first block member backing surface and said movement adapting said second block member at the end of its outward movement to provide with said backing surface a continuation of said slots to slidably receive said blade and at the end of its inward movement being adapted to contact and clamp a lengthwise extending edgc portion located immediately below the sharpened cutting edge of the other opposite one side of said blade in a longitudinally tensionless free manner between said backing and clamping surfaces and to properly position the said cutting edge thereof;

(c) opening means operative on said clamping member when unclamped to force said clamping member outwardly; and (d) a manually operated rotatable camming member mounted on said holder, said camming member being effective when rotated in one direction to cam said second block member and pivot said second block member about the axis of said rocker arm in said slight outward movement so as to effect said slot and release said blade for replacement and in an opposite direction to cam said second block member in said slightly inward movement against the force of sAid opening means so as to clamp at least said edge portion of said blade while leaving the said sharpened cutting edge precisely positioned for cutting.

23. A microtome disposable blade holder as claimed in claim 22 wherein said first block member comprises a base member and a pair of removable end members forming portions of said end portions.

24. A microtome apparatus as claimed in claim 22 wherein:

(a) said backing surface comprises a concave surface;
(b) said clamping surface comprises a convex surface; and
(c) said camming member is effective in said slightly inward movement of said second block member to clamp and curve the said cutting edge portion of said blade around a longitudinal axis between said backing and clamping surfaces.

25. A microtome apparatus as claimed in claim 25 wherein:

(a) said backing surface comprises a flat surface;
(b) said clamping surface comprises a flat surface; and (c) said camming member is effective in said slightly inward movement of said second block member to clamp the said edge portion of said blade flat between said backing and clamping surfaces.

26. A microtome apparatus as claimed in claim 25 including a pair of insert members removably secured on the ends of said first block member and formed for effectively enlarging the size of said end portions and for being received and clamped in a corresponding size of said knife clamp.

27. A microtome apparatus as claimed in claim 22 wherein said opening means comprises spring means mounted below said clamping and backing surfaces and above said rocker arm.

28. A microtome as claimed in claim 22 including an anti-roll plate assembly with a base member, magnet securing means embedded in said base member and means on said blade clamping member for precisely locating said base member thereon and utilizing said magnet securing means for securing said anti-roll assembly on said holder.

29. A microtome apparatus as claimed in claim 28 wherein said magnet securing means comprises a magnet embedded in said base member.

30. A microtome apparatus as claimed in claim 28 wherein said means on said blade clamping member for precisely locating said base member thereon includes a pair of holes on the outer surface of said blade clamping member and said anti-roll assembly includes a pair of pins mating said holes and locating said base member.

31. A microtome apparatus as claimed in claim 28 wherein said means on said blade clamping member for precisely locating said base member thereon includes a pair of slots on the outer surface of said blade clamping member and said anti-roll assembly includes a pair of pins mating said slots and locating said base member.

32. A microtome apparatus as claimed in claim 28 wherein said magnet securing means comprises a ferromagnetic plate embedded in said base member and said means on said blade clamping member for precisely locating said base member thereon includes a magnet embedded therein and attracted to said ferromagnetic plate.

* * * * *

UNITED STATES PATENT AND TRADEMARK OFFICE
CERTIFICATE OF CORRECTION

PATENT NO. : 4,700,600

DATED : October 20, 1987

INVENTOR(S) : John E. P. Pickett

It is certified that error appears in the above-identified patent and that said Letters Patent is hereby corrected as shown below:

Column 16, Line 6 correct "bahking" to read --backing--. (PTO error)

Column 16, line 47 correct "sAid" to read --said--. (PTO error)

Signed and Sealed this

First Day of March, 1988

Attest:

DONALD J. QUIGG

Attesting Officer

Commissioner of Patents and Trademarks